(12) United States Patent
Lum et al.

(10) Patent No.: US 6,391,005 B1
(45) Date of Patent: *May 21, 2002

(54) APPARATUS AND METHOD FOR PENETRATION WITH SHAFT HAVING A SENSOR FOR SENSING PENETRATION DEPTH

(75) Inventors: Paul Lum, Los Altos; Hewlett E. Melton, Jr., Sunnyvale; Tad Decataur Simons, Palo Alto; Michael Greenstein, Los Altos, all of CA (US)

(73) Assignee: Agilent Technologies, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/050,853

(22) Filed: Mar. 30, 1998

(51) Int. Cl.[7] .................................................. A61M 5/00
(52) U.S. Cl. ..................... 604/117; 604/500; 604/65; 604/66; 604/272; 600/506; 600/547
(58) Field of Search ................................. 604/117, 116, 604/49, 51, 52, 65, 66, 67, 264, 272, 22, 46, 500, 503, 165.04; 600/382, 398, 399, 506, 547, 576, 583, 300, 554, 373, 546, 582, 568, 372; 606/181

(56) References Cited

U.S. PATENT DOCUMENTS

| | | | | |
|---|---|---|---|---|
| 2,763,935 A | * | 9/1956 | Whaley et al. | 33/169 |
| 3,712,292 A | | 1/1973 | Mielke, Jr. | 128/2 G |
| 3,938,526 A | * | 2/1976 | Anderson et al. | 128/303.1 |
| 3,971,365 A | * | 7/1976 | Smith | 128/2.17 |
| 4,139,011 A | | 2/1979 | Benoit et al. | 128/329 |
| 4,184,486 A | | 1/1980 | Papa | 128/642 |

(List continued on next page.)

FOREIGN PATENT DOCUMENTS

| EP | 823239 A2 | 11/1998 | A61B/5/05 |
|---|---|---|---|
| GB | 1558111 | 12/1979 | A61B/5/05 |

OTHER PUBLICATIONS

DE 44 20 232 AS1—Dec. 14, 1995.

FR 2622457—May 5, 1989—A61M5/20.

Edited by Berardesca M.D. et al., "Bioengineering of the Skin: Methods and Instrumentation", 1995, pp. 1–13, CRC Press, Boca Raton, New York.

*Primary Examiner*—Richard K. Seidel
*Assistant Examiner*—Cris L Rodriguez

(57) ABSTRACT

An apparatus having a shaft that can sense the depth of penetration, for penetrating into an object (the substrate). The substrate being penetrated has impedance that varies according to the depth under a surface of the substrate. The shaft has a tip for penetration and has conductive ends near to the tip of the shaft. A change of impedance of material of the object between the conductive ends can be sensed to provide information on the depth of penetration. A processor can be provided external to the object being penetrated by the shaft to gather and process the impedance information to determine whether the desired depth has been achieved.

20 Claims, 5 Drawing Sheets

U.S. PATENT DOCUMENTS

| | | | |
|---|---|---|---|
| 4,203,446 A | 5/1980 | Hofert et al. | 128/329 |
| 4,224,949 A * | 9/1980 | Scott et al. | 128/734 |
| 4,299,230 A * | 11/1981 | Kubota | 604/117 |
| 4,356,826 A * | 11/1982 | Kubota | 604/117 |
| 4,411,266 A * | 10/1983 | Cosman | 128/303.18 |
| 4,469,110 A | 9/1984 | Slama | 128/770 |
| 4,535,773 A * | 8/1985 | Yoon | 604/51 |
| 4,561,445 A * | 12/1985 | Berke et al. | 128/642 |
| 4,577,630 A | 3/1986 | Nitzsche et al. | 128/314 |
| 4,712,548 A | 12/1987 | Enstrom | 128/314 |
| 5,133,730 A | 7/1992 | Biro et al. | 606/182 |
| 5,196,025 A | 3/1993 | Ranalletta et al. | 606/182 |
| 5,211,652 A | 5/1993 | Derbyshire | 606/182 |
| 5,266,359 A | 11/1993 | Spielvogel | 427/388 |
| 5,318,583 A | 6/1994 | Rabenau et al. | 606/182 |
| 5,318,584 A | 6/1994 | Lange et al. | 606/181 |
| 5,395,387 A | 3/1995 | Burns | 606/181 |
| 5,571,132 A | 11/1996 | Mawhirt et al. | 606/167 |
| 5,853,373 A * | 12/1998 | Griffith et al. | 600/554 |

* cited by examiner

APPARATUS AND METHOD FOR PENETRATION WITH SHAFT HAVING A SENSOR FOR SENSING PENETRATION DEPTH

FIELD OF THE INVENTION

The present invention is related to techniques for penetration of an object with a shaft and more particularly to apparatuses and methods for determining the penetration depth of a hypodermic needle.

BACKGROUND

When inserting a long structure into an object, such as a needle into the tissue of a patient, it is often necessary to know how deep the penetration is. Penetration past the required depth for a desired result wastes effort and causes undue discomfort to the patient. Often the information is needed in a short time because further penetration may cause unnecessary damage to the object and it is desirable to stop the penetration once a predetermined depth is reached. For example, the analysis and quantification of blood components is an important diagnostic tool for better understanding the physical condition of a patient and blood samples need to be obtained by inflicting a wound by a needle or lancet. Inserting the needle or lancet to a depth deeper than necessary produces excessive pain and trauma to the skin tissue. In patients such as diabetics, who have to sample blood often, any excessive pain or tissue trauma is a disincentive to comply with the blood sampling routine.

The skin is consisted of two layers—the epidermis and the dermis. The capillary structures connected to the arterial and venous vascular beds rise vertically and are located in the dermis layer. The neural sensors such as Meissner's corpuscles and free nerve endings are also located in the dermis. Layers of subcutaneous tissues lie below the dermis. The supply arterial and venous capillaries are located laterally in this tissue bed. There is also adipose tissue interleaved with afferent and efferent nerve fibers along with their associated sensors interwoven within the vascular bed. The thicknesses of these tissue layers differ from individual to individual. Currently, commercially available needle or lancet for puncturing skin have preset penetration depth based on experimental data from lancing, Thus, there is no certainty that the optimal depth of penetration is reached every time such a needle or lancet is used. To avoid unsuccessful blood sampling due to inadequate depth, a patient often overpenetrates the skin, causing unnecessary pain.

What is needed is a needle or lancet for sampling blood that can be used for inserting to the optimal depth without over or under penetration. Similarly, there is a need in other penetration applications for inserting a long shaft into an object without over or under penetration.

SUMMARY

In the present invention, the depth of penetration of an elongated structure into an object is determined by an impedance sensor that senses the impedance of the material penetrated by the elongated structure at the tip of the elongated structure.

In one aspect, the present invention provides an apparatus having a shaft for penetration into an object which has impedance that varies according to the depth under a surface of the object. The apparatus contains a shaft that includes a shaft body having a tip for penetration and two conductive ends near the tip. The two conductive ends are near the tip such that a change of impedance of the material of the object sensed between the conductive ends will provide information on whether the desired depth of penetration has been reached.

This invention is especially applicable in obtaining blood from a patient by puncturing the skin because a shaft of the present invention takes advantage of the electrical impedance differences between deeper layers of skin tissue relative to the more shallow upper layer. The impedance can be monitored by, for example, a metallic needle that pierces the layers of skin tissue. When the needle initially penetrates into the outer epidermis and dermis layers of the skin, an initial high impedance is seen. A decline in the impedance is observed as the needle approaches the adipose layer.

Using the apparatus, including the shaft of the present invention, optimal penetration into an object that has electrical impedance which varies with penetration depth can be achieved. In the case of obtaining blood from a patient by inserting a needle into the skin, this can minimize the trauma and pain of overpenetration, as well as avoid the frustration and pain of unsuccessful blood sampling because of inadequate penetration. Such reduction of discomfort and tissue damage can significantly improve the compliance of patients with a blood sampling routine, for example.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

In one aspect, the present invention provides a technique for sensing the depth of penetration when inserting a shaft into a body. As used herein, the term "shaft" refers to an object with a generally elongated body with a tip for penetrating the body of interest. The body of the shaft, depending on the application, can be rigid or somewhat flexible. Preferably, the tip has a relative sharp point or beveled lancet to facilitate penetration. The point is adequate sharp such that the shaft can be pushed into the body without the need for passing along a preexisting hole. The body of the shaft can have a cross section that is round or non-round (e.g., having a rectangular cross section). As an example, a needle-sized shaft suitable for hypodermic insertion is described in the following embodiments. It is to be understood that other non-hypodermic shafts, including shafts for non-medical purposes, can be made and used according to the present invention.

Needles and Lancets

Figure 1:
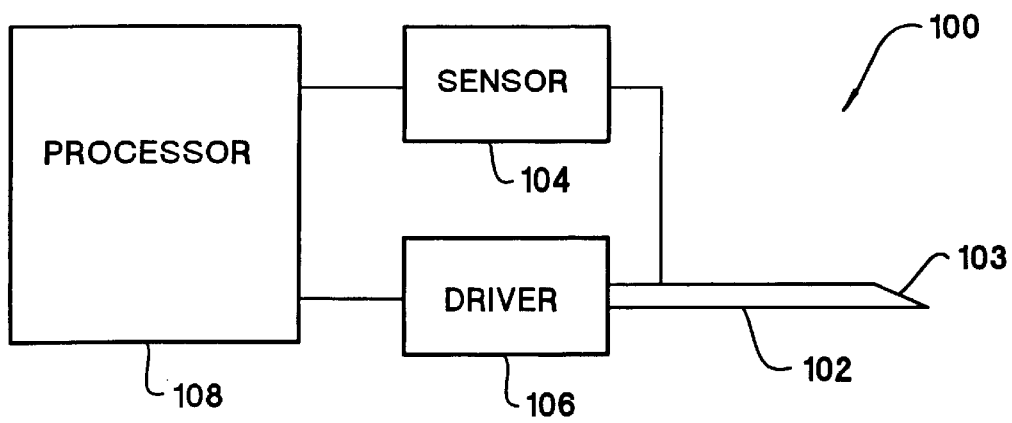
FIG. 1 shows an embodiment of an apparatus of the present invention.

FIG. 1 shows an embodiment of an apparatus for driving a shaft for penetrating skin according to the present invention. In FIG. 1, the apparatus 100 includes a shaft 102 (e.g., a needle or lancet) with conductive ends for sensing the impedance of tissue about the tip 103 of the shaft 102. An impedance sensor 104 (which includes electrical circuitry that senses impedance) electrically connected to the conductive ends senses the electrical impedance. Electrical devices and circuits that sense the electrical impedance between two points, e.g., in a material or in a circuit, are known in the art. An electrically controlled driver 106 drives the shaft 102 to penetrate the skin of the patient and tissue under it, which can be referred to as the "substrate" of penetration. The driver 106 is controlled by a processor 108, which stops the driver when the impedance sensor 104 senses an impedance change indicating the desired penetration has been achieved.

Figure 2A:
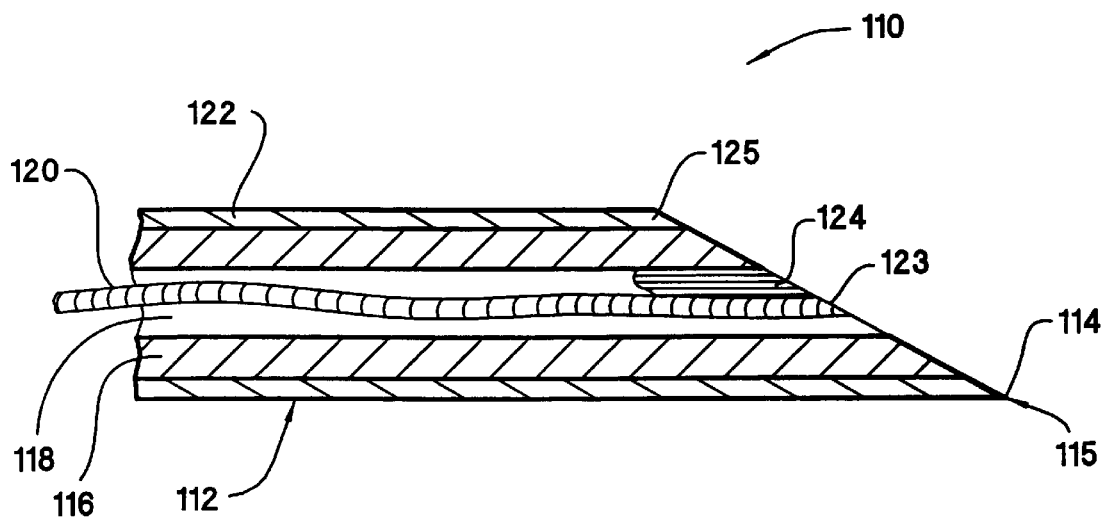
FIG. 2A and 2B show an embodiment of a shaft of the present invention.
Figure 2B:
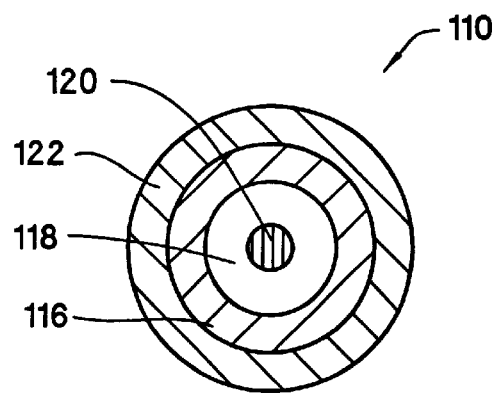

For illustration, FIG. 2A shows an embodiment of a portion of a hypodermic needle 110 that can be used in the present invention, e.g., as the shaft 102 in the apparatus 100. FIG. 2A is a sectional view along the axis of the hypodermic needle 110 and FIG. 2B shows a cross section of the hypodermic needle 110. The hypodermic needle 110 includes a stiff shaft body 112 having a sharp tip 114 at the distal end 115 for penetration into tissue. The shaft body 112 has a stiff, electrically non-conductive (e.g., polymeric, such as polyimide) tubing 116 with a central lumen 118 at the axis of the tubing 116. An electrically conductive (e.g., metallic tungsten) wire 120 located at the approximate axis of the tubing 116 extends from the sharp tip 114 proximally. The tungsten wire 120 has a distal conductive end 123 proximate to the distal end 115. As used herein, the term "distal" refers to the direction towards the object (e.g. the patient's skin) when the needle is about to penetrate the object and the term "proximal" refers to the direction opposite to that of "distal," therefore away from the object. An electrically conductive coating 122 (e.g., chrome/gold plated coating) is disposed on the outer surface of the nonconductive tubing 116 and has conductive end 125 at the tip 114. An adhesive 124 (see FIG. 2A), preferably electrically conductive, such as a silver epoxy, is used to attach the distal end of the electrically conductive wire 120 to the distal end 115 of the hypodermic needle 110.

Furthermore, if desired, a chamber or reservoir can be connected to the lumen 118 for collection of the fluid that may conduct through the lumen. This chamber or reservoir can be a nonconductive bag, a syringe, other tubings connected to the lumen, and the like.

Such a hypodermic needle can be made by, for example, electroplating a polyimide tubing to deposit the electrically conductive coating on the polyimide tubing and inserting, for example, a tungsten wire into the polyimide tubing and affixing an end of the wire to the distal end of the hypodermic needle with a silver epoxy. The distal end can be sharpened after all the conductive materials are in place. The proximal end of the electrically conductive wire 120 and the proximal end of the electrically conductive coating 122 can be connected to the impedance sensor 104 in the apparatus 100, or other similar equipment for sensing the penetration depth of the hypodermic needle 110. Other suitable materials for making the electrically conductive coating include, for example, silver, nickel, platinum, titanium, and tungsten. Materials suitable for making the electrically conductive wire include, for example, silver, nickel, platinum, titanium, gold, copper, aluminum, and tungsten.

Figure 3:
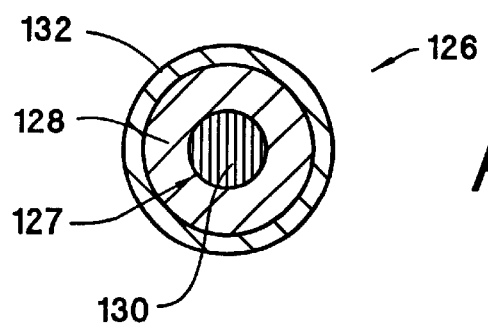
FIG. 3 shows another embodiment of a shaft of the present invention.

In another embodiment, as shown in FIG. 3, a solid needle assembly 126 can be made by filling the lumen 127 of a hollow nonconductive needle 128 with a conductive material 130 and coating on the non-conductive needle with a metallic coating 132. The resultant elongated structure can be modified to produce a sharp tip. Alternatively, a non-conductive material can be coated on a stiff metallic wire and then an outer coat of conductive metal can be coated on the non-conductive material to form a solid needle. Such a needle will have a structure similar to that shown in FIG. 3, which shows a cross section of the shaft.

To further stiffen a needle shaft for penetration, the needle having conductors leading to the distal end can be further coated with a material that provides additional rigidity. Many hard materials, such as metals or alloys are known in the art. An example of a material suitable for providing such additional rigidity is titanium nitride.

Figure 4:
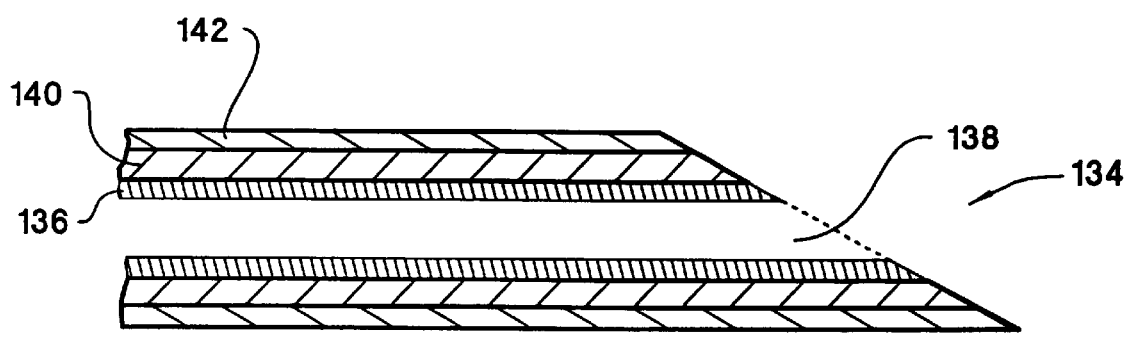
FIG. 4 shows yet another embodiment of a shaft of the present invention.

FIG. 4 shows another embodiment of a hypodermic needle of the present invention. In the hypodermic needle 134 shown in FIG. 4, an inner electrically conductive tubing 136 with a lumen 138 has a coating of a non-conductive material 140 electrically insulating the inner tubing 136 from an electrically conductive coating 142 that is more remote from the axis. This hypodermic needle 134 can be made by coating, e.g., a steel needle with a non-conductive material and then sputtering a metallic coating on the electrically non-conductive material and further electroplating to form the outer electrically conductive coating 142.

Figure 5A:
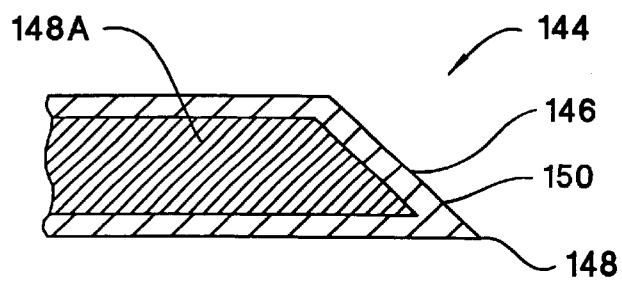
FIGS. 5 A and 5B show a lancet of the present invention.
Figure 5B:
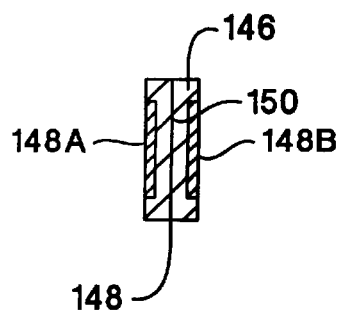

FIGS. 5A (a side view) and 5B (a front view) show yet another embodiment in which a shaft suitable for inserting into the skin of a patient has conductors for sensing impedance of the tissue surrounding the tip of the shaft. The shaft 144 has a rectangular cross section (see the front view of FIG. 5B) and has a central part 146 made of a stiff non-conductive material extending lengthwise along the shaft 144 sandwiched between two conductors 148A and 148B. The central part has a sharp tip 148 leading into a sharp edge 150 for cutting into a skin. Such a shaft can be used as a lancet for cutting a wound in the skin to yield blood.

Mechanisms for Driving the Shaft

A wide variety of drivers can be used to drive the shaft (including needles, lancets, blades) of the present invention. Such drivers can be electrically controlled such that when the desired depth has been achieved, the driver can be stopped, preferably, automatically. In this way, the depth of penetration can be optimized so that minimal penetration is used to achieve the desired result, such as drawing blood from a patient with the infliction of a minimal amount of pain and wound size. Examples of mechanisms that can be used for the driver include pneumatic, electromechanical, and piezoelectric mechanisms.

Figure 6A:
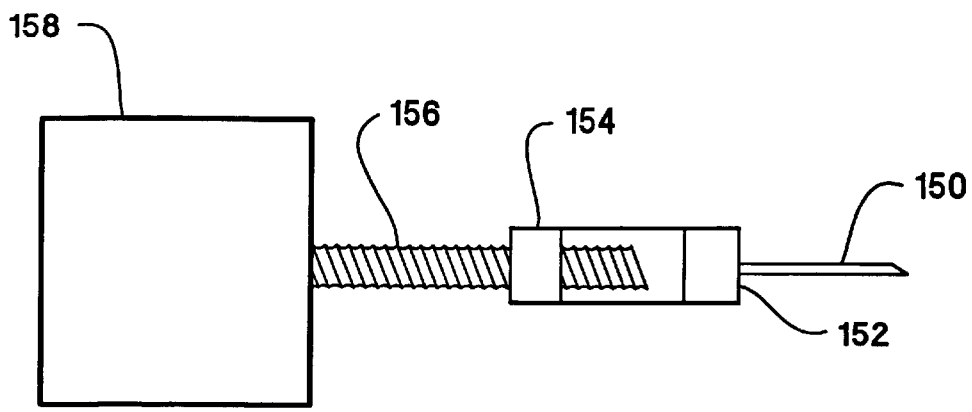
FIGS. 6A and 6B show apparatuses including an embodiment of a driver for driving a shaft according to the present invention.

FIG. 6A shows an apparatus with a driver for driving a shaft continually with a threaded mechanism. In the embodiment of FIG. 6A, the shaft 150 is affixed to a base 152 rigidly linked to a sleeve 154, which mates with a threaded rod 156. The threads of the sleeve 154 are so engaged with the threads of the threaded rod 156 such that the rotation of the threaded rod 156 will move the sleeve 154 along the threaded rod 156 axially. Therefore, a motor 158 that drives the rotation of threaded rod 156 in a direction (e.g. clockwise rotation) will drive the forward motion of the shaft 150 in the distal direction. Stopping the motor 158 will stop the forward advance of the shaft 150. Holding the motor 158 at a fixed position relative to the object to be penetrate and controlling the motor will control the depth of penetration of the shaft 150. Furthermore, the motor 158 can be driven to advance incrementally in an intermittent, stepwise fashion. If desired, the motor 158 can be operated to rotate in two directions to provide both forward and backward motion for advancing and withdrawing the shaft 150.

Figure 6B:
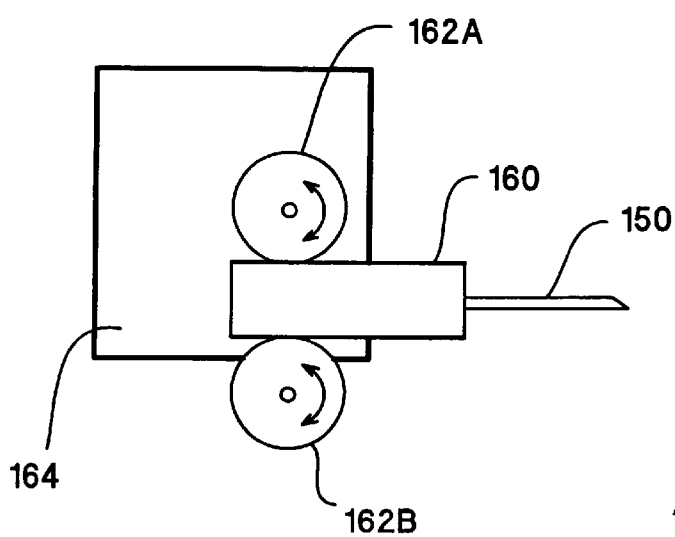

FIG. 6B illustrates another embodiment in which the shaft can be driven to advance continually. In this embodiment, a shaft 150 (e.g., a needle) is affixed to a base 160. The base 160 (and therefore the shaft 150) is driven to move in the forward, i.e., distal, direction by a rotor 162A that engages the base 160 on the side such that rotating the rotor 162A will move the base 160 and shaft 150 distally. The rotor 162A is driven by the a motor 164. Another rotor 162B engages the base 160 on a side opposite that of the rotor 162A for support. Either rotor 162A or rotor 162B can be an idler rotor. The rotors 162A and 162B can engage the base 160 by means of gears or by friction.

Figure 7A:
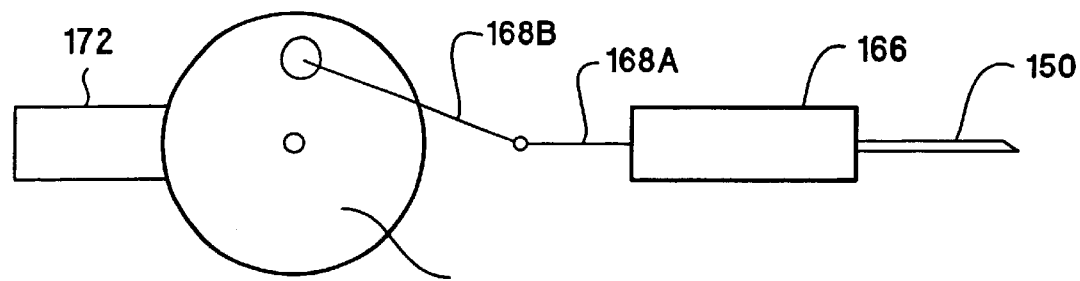
FIG. 7A shows an apparatus including an embodiment of a driver for driving a shaft.

FIG. 7A shows an embodiment of a shaft-penetration apparatus of the present invention with reciprocative action for inserting the shaft into a body. A shaft 150 is affixed to a link 166 actuated by linking arms 168A, 168B. The linking arms 168A and 168B are pivotably connected to each other. The linking arm 168B is pivotably connected off center to the rotor 170, which in turn is driven by motor 172. Thus, the rotation of the rotor 170 results in a back and forth reciprocative movement of the linking arms 168A, 168B, which is translated to the shaft 150. In addition, the whole system can be move steadily forward distally to advance the shaft 150 distally.

Figure 7B:
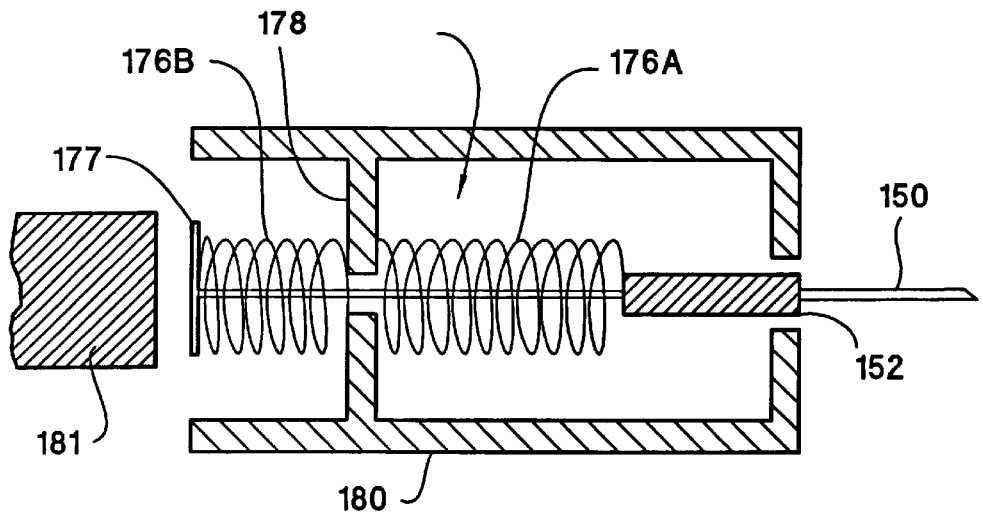
FIG. 7B shows an apparatus including a portion of an embodiment of a driver for driving a shaft.

FIG. 7B shows an embodiment of a spring mechanism 174 that can be used, e.g., as the link 166. The shaft 150, supported on a base 152 is held by the spring mechanism 174, which consists of a primary spring coil 176A and a secondary spring coil 176B. The primary spring coil 176A and secondary spring coil 176B are each held at one end by a ledge 178 of a housing 180, which houses the spring coils and part of the base 152. An end disk 177 is disposed at the proximal end of the spring coils 176A, 176B and affixed to the base 152 by a rigid rod 180 that extends through the axis of the spring coils 176A, 176B. A hammer 181 (shown in portion) can be used to impact the end disk 177, which drives the shaft 150 forward by means of rigid rod 180. After the impact, the springs 176A and 176B can move the shaft backward. It is noted that one of the springs 176A and 176B is optional and an alternative is to use only one of them.

Figure 8:
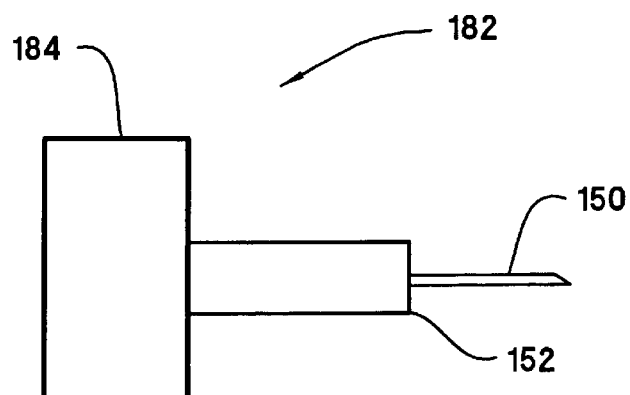
FIG. 8 shows an apparatus including a portion of a piezoelectric driver for driving a shaft.

FIG. 8 shows an example of a piezoelectric driver 182 for producing a reciprocative motion to drive a shaft for penetration. As in the aforementioned embodiments, a shaft 150 is affixed to a base 152, which is attached to a piezoelectric vibrator 184. When energized electrically, the piezoelectric vibrator 184 will vibrate to move the base 152 and the shaft 150 in a forward-backward motion. This whole vibrating driver system 182 can be advanced forward. Technique for making and using piezoelectric vibrators are known in the art and can be easily adopted for driving a shaft based on the present disclosure.

Figure 9:
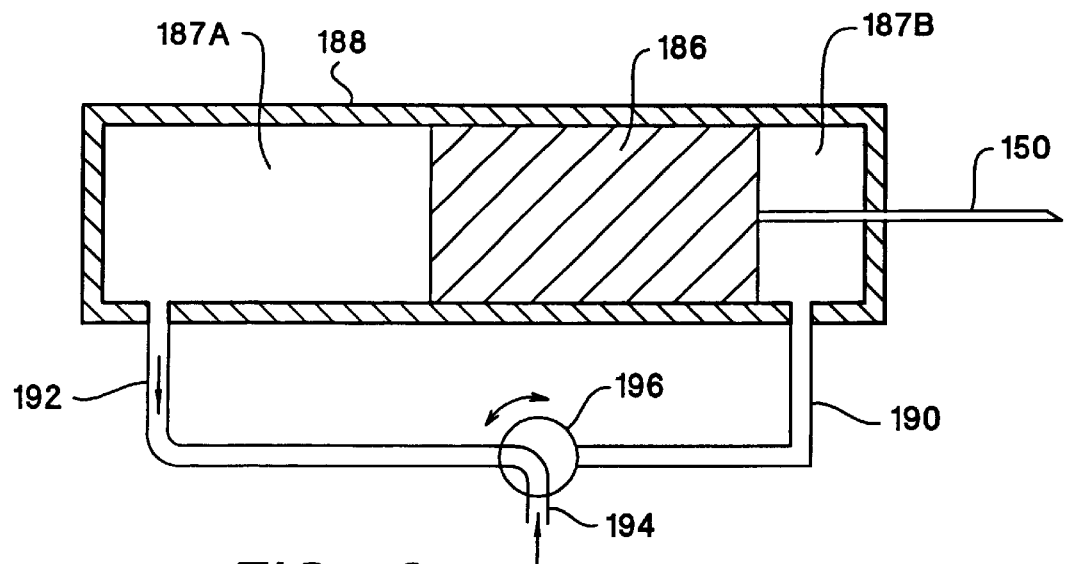
FIG. 9 shows an apparatus including a portion of a fluid-driven driver for driving a shaft.

FIG. 9 shows a fluid mechanism for driving a reciprocative motion for driving a shaft. Here, a shaft 150 is attached to a piston 186 that is allowed to slide inside a chamber (shown in the figure including the chamber 187A, chamber 187B and the volume occupied by the piston 186) in a piston housing 188. A distal fluid conduit 190 distal to the piston 186 allows a fluid to enter the chamber 187B to drive the piston proximally, i.e., in a direction opposite to the distal direction. At the same time, preferably, a proximal fluid conduit inlet 192 proximal to the piston 186 can allow fluid to escape to facilitate the movement of the piston without building excessive pressure in the chamber 187A. Conversely, the proximal fluid conduit 192 can allow fluid to enter the chamber 187A to drive the piston distally while the distal fluid conduit 190 allows fluid to escape. A common fluid inlet conduit 194, connected to a multi-way valve 196 (e.g., three-way valve) can allow fluid to enter the proximal fluid conduit 192 or distal fluid conduit 190. Alternately admitting fluid into the chamber 187 proximal and distal tithe piston while at the same time releasing fluid on the opposite side of the chamber will result in a reciprocative motion. To effect a progressive advance of the shaft 150 at the distal direction, over time, more fluid can enter the proximal conduit 192 than the distal fluid conduit 190. Optionally, one or both of the chambers 187A and 187B can be kept close to the environmental pressure so as to not put too much stress on the structure of the mechanism. Alternatively, the whole mechanism shown in FIG. 9 can be advanced while it is reciprocatively moving. A gas or a liquid can be used as the fluid for entering the chamber 187 to drive the progressive movement of the shaft 150.

The present invention can also find application in which the shaft advances in a sawing action, as that described in a copending application Ser. No. 09/050,748, Inventors: Ganapati Mauze, et al., entitled "APPARATUS AND METHOD FOR INCISING") submitted on the same day and assigned to the same assignee as the present application. Said copending application is incorporated by reference in its entirety herein. An example of such an apparatus has an elongated structure for conducting blood with an outer tube and an inner tube. The tubes associated with each other in concentric, close proximity with low friction between them so that one can slide on the other freely. The distal ends of the tubes each has a circular sharp cutting edge. The tubes are driven to move longitudinally reciprocatively such that alternately the sharp ring-shaped end of the outer tube is more distal than the end of the inner tube and the sharp ring-shaped end of the inner tube is more distal than the end of the outer tube. In this way, the elongated structure can penetrate the tissue by a sawing action by the two tubes.

Figure 10:
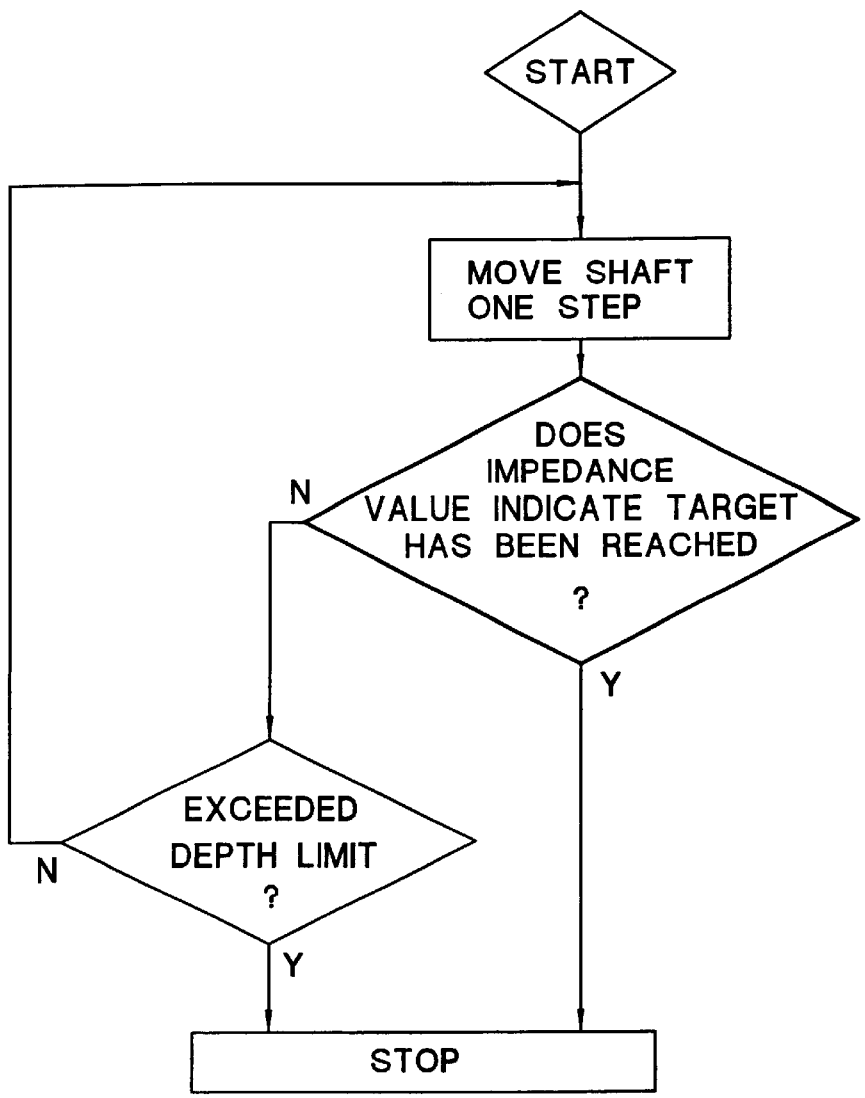
FIG. 10 shows a flow diagram for an algorithm for controlling the driver for driving a shaft according to the present invention.

The driving mechanism for driving the shaft (e.g., needle, lancet, and the like) of the present invention can be controlled by feedback electronics circuits that inhibit further shaft penetration once a proper depth of fluid material has been sensed. Typically, such a control system would be placed in the processor shown in FIG. 1. A control algorithm for such a control system is illustrated by an exemplary flow diagram shown in FIG. 10. In this algorithm, once initiated, the driver will move the shaft one step at a time to advance an incremental distance until either the impedance measured indicate that the shaft has reach the target area (e.g. blood in capillary bed by a needle penetrating skin) or until the predetermined depth of penetration has been reached, at which point the driver will be stopped by the control circuitry. Whether the proper depth has been reached by the shaft can be determined by the magnitude of the change in impedance or the magnitude of the impedance itself. The selection of impedance values or jump values can be done by one skilled in the art. A processor can be provided external to the object that is being penetrated by the shaft for gathering and processing the impedance information to determine whether the desired depth has been achieved, as well as to control the movement of the shaft. Electrical devices and electrical circuits for processing information, controlling drivers, as well as those for sensing electrical impedance are known in the art. Such devices and circuits could include computers or microprocessors.

To use the apparatus of the present for the optimal benefit, preferably, the change in impedance with the depth of penetration is determined experimentally. After a few times of sampling, the apparatus can be adjusted to set the depth of insertion in relation to impedance changes to fit the particular preferences (e.g., penetration depth and sample volume) of that individual. Another way would be to obtain impedance data versus depth specifically for an individual patient and, after taking data from a plurality of blood samples, use the resultant data for setting the depth of penetration for future blood samples.

Although the preferred embodiment of the present invention has been described and illustrated in detail, it is to be understood that a person skilled in the art can make modifications within the scope of the invention. For example, it is understood that the present invention can be applied in a wide variety of medical or nonmedical areas, e.g., drilling in the ground for water, gas, petroleum, etc.

What is claimed is:

1. An apparatus for penetrating into tissue which has impedance that varies according to the depth of tissue, comprising:
    a shaft comprising:
        (i) a shaft body with a tip for penetration; and
        (ii) first and second conductors proximate to the tip such that a change of electrical impedance of material of the between the first and second conductors can be sensed to provide information on the depth of penetration; and
    electronic circuit associated with the shaft for determining the change in electrical impedance between the first and second conductors, said electronic circuit providing an electrical signal to automatically drives said shaft as a function of said electrical impedance.

2. The apparatus according to claim 1 further comprising a first conductor line leading from the first conductors to the electronic circuit and a second conductor line leading from the second to the electronic circuit, the shaft comprising an electrical insulator interposing between the first conductor and the second conductor.

3. The apparatus according to claim 2 wherein the first conductor line is on one side of the shaft and the second conductor line is on a second side of the shaft to prevent the two conductor lines from electrically contacting each other.

4. The apparatus according to claim 1 further comprising a channel in the shaft extending from the tip for conducting fluid from the tip through the shaft.

5. The apparatus according to claim 4 wherein the shaft has a center line and the second conductor is proximate to the central line and the shaft comprising an electrical insulator interposing between the first conductor and the second conductor.

6. The apparatus according to claim 5 wherein the electrical insulator is a tube, the first conductor is a conductive layer encircling the insulator tube, and the second conductor extending inside the insulator tube, and wherein the electronic circuit is located remote from the tip.

7. The apparatus according to claim 4 wherein the shaft body comprises a metallic tube, an electrically insulating layer coated on the metallic tube and a conductor layer coated on the electrically insulating layer, the conductor layer being in electrical communication with the first conductor and the electronic circuit and the metallic tube being in electrical communication with the second conductor and the electronic circuit, and wherein the electronic circuit is located external to the tissue when the shaft has penetrated the tissue.

8. The apparatus according to claim 4 further comprising a reservoir operatively connected to the shaft in fluid communication with the channel to receive fluid therefrom.

9. The apparatus according to claim 1 wherein the shaft body has a size of a hypodermic needle for penetrating the skin of a patient.

10. The apparatus according to claim 1 further comprising a mechanical driver operatively associated with the shaft for driving the shaft into the body by incremental steps.

11. An apparatus having a shaft for penetration into tissue which has impedance that varies according to the depth of tissue penetrated comprising:
    (a) a shaft having a size of that of a hypodermic needle, with a sharp tip for penetration;
    (b) An impedance sensor connected to the shaft and including: first and second conductors proximate to the sharp tip such that a change of impedance of material of the tissue between the first and second conductors can be sensed to provide information on the depth of penetration; electronics for determining said change in impedance; first and second lines extending along the shaft to connect the conductors to the electronics; and an electrical insulator interposing between the first conductor and the second conductor; and
    (c) mechanical driver operatively contacting the shaft for incrementally driving the shaft, the driving action being affected by said change of impedance.

12. A method for driving a shaft into tissue comprising:
    (a) driving a shaft to penetrate into tissue having a surface and material with electrical impedance varying with depth of tissue penetrated; and
    (b) sensing the electrical impedance of the material in the tissue proximate the tip of the shaft during penetration to determine whether desired depth has been achieved and automatically modifying the driving action of an electrically controlled driver with an electrical signal based on the electrical impedance sensed by an electrical circuit.

13. The method according to claim 12 further comprising driving the shaft incrementally with a driver.

14. The method according to claim 13 further comprising reciprocatively driving the shaft to penetrate the tissue.

15. The method according to claim 12 further comprising stopping the driving action when a desired depth of penetration has been sensed.

16. The method according to claim 12 wherein the shaft has a channel therein and further comprising allowing fluid to flow from the tissue through the shaft to sample the fluid.

17. A method for inserting a needle-sized shaft through the skin and underlying tissue comprising:
    (a) driving a needle-sized shaft to penetrate into said tissue through the skin;
    (b) electrically sensing the electrical impedance of said tissue from an electronic circuit to determine whether desired penetration depth has been achieved; and
    (c) automatically stopping the advance of the needle-sized shaft when the desired depth has been achieved based on an electrical signal provided to an electrically controlled driver by said electronic circuit.

18. The method according to claim 17 further comprising using an electrical driver to drive the needle-sized shaft incrementally and electrically stopping the electrical driver when the desired depth has been achieved.

19. An apparatus having a shaft for penetrating into tissue which has impedance that varies according to the depth of tissue penetrated comprising:

a shaft comprising:
- (i) a shaft body with a tip for penetration; and
- (ii) first and second conductors proximate to the tip such that a change of impedance of material of the tissue between the first and second conductors can be sensed to provide information on the depth of penetration; and a mechanical driver associated with the shaft for driving the shaft into the body by incremental steps.

20. A method for driving a shaft into ti'sue, comprising:
- (a) driving a shaft having a tip to penetrate into tissue having a fluid therein;
- (b) sensing the impedance of the material in the tissue proximate the tip of the shaft during penetration to determine whether desired depth has been achieved and automatically modifying the driving action based on the impedance sensed by an electronic circuit, said electronic circuit providing an electrical signal to modify said driving action; and allowing fluid to flow from the tissue through a channel in the shaft to sample the fluid.

* * * * *